(12) United States Patent
Lin (10) Patent No.: US 8,076,531 B2
(45) Date of Patent: Dec. 13, 2011

(54) TRANSGENIC ANIMAL WITH MONOCYTE CHEMOTACTIC PROTEIN 1 PROMOTER

(75) Inventor: Kurt Ming-Chao Lin, Zhunan Town (TW)

(73) Assignee: National Health Research Institutes, Zhunan Town, Miaoli County (TW)

( * ) Notice: Subject to any disclaimer, the term of this patent is extended or adjusted under 35 U.S.C. 154(b) by 0 days.

(21) Appl. No.: 12/626,227

(22) Filed: Nov. 25, 2009

(65) Prior Publication Data

US 2011/0126297 A1 May 26, 2011

(51) Int. Cl.
*A01K 67/00* (2006.01)
*G01N 33/00* (2006.01)
*C07H 21/04* (2006.01)
*C12N 15/00* (2006.01)

(52) U.S. Cl. .............................. 800/13; 800/3; 536/23.1
(58) Field of Classification Search ........................ None
See application file for complete search history.

(56) References Cited

U.S. PATENT DOCUMENTS

| 5,817,911 | A  | * | 10/1998 | Williams et al. | 800/9 |
| 6,217,847 | B1 |   | 4/2001  | Contag          |       |
| 7,595,430 | B2 | * | 9/2009  | Jayakrishna     | 800/3 |
| 2006/0277613 | A1 | * | 12/2006 | Gambhir et al. | 800/8 |

OTHER PUBLICATIONS

Boekhoudt et al. Communication between NF-kB and Sp1 controls histone acetylation within the proximal promoter of the monocyte chemoattractant protein 1 gene. J. Immunology 170:4139-4147, 2003.*
Desai et al. Nitric oxide modulates MCP-1 expression in endothelial cells: Implications for the pathogenesis of pulmonary granulmatous vasculitis. Inflammation 27:213-223, 2003.*
Carlsen, et al., "*In Vivo Imaging of NF-kB Activity*[1]", The Journal of Immunology, 2002, 168:1441-1446.
Rajasekaran, et al., "*Detection of Experimentally Induced Pulmonary Granuloma Inflammation in Monocyte Chemoattractant Protein-lReporter Mice*", Mol Imaging Biol (2009) D01: 10.1007/s11307-009-0261-9.
Tsuchiyama, et al., "*Enhanced antitumor effects of a bicistronic adenovirus vector expressing both herpes simplex virus thymidine kinase and monocyte chemoattractant protein-1 against hepatocellular carcinoma*", Cancer Gene Therapy (2003) 10, 260-269.

* cited by examiner

*Primary Examiner* — Quang Nguyen
(74) *Attorney, Agent, or Firm* — Occhiuti Rohlicek & Tsao LLP (57) ABSTRACT

The present invention relates to a transgenic animal, which comprises in its genome a recombinant polynucleotide encoding one or more reporter proteins and a monocyte chemotactic protein-1 (MCP-1) promoter, wherein the one or more reporter proteins are expressed under the control of the MCP-1 promoter. A method for monitoring endogenous expression of MCP-1 in vivo is also provided, which is useful for identifying a regulator of the expression of MCP-1 or an anti-inflammatory agent.

9 Claims, 8 Drawing Sheets

-510 ttacacaatcctacagttctgctaggcttctatgatgctactattctgc
atttgaatgagcaaatggatttaatgcattgtcagggagccggccaaag
cttgagagctccttcctggctgggaggccccttggaatgtggcctgaag
gtaagctggcagcgagcctgacatgctttcatctagtttcctcgcttcc
ttccttttctgcagttttcgcttcacagaaagcagaatccttaaaaata
accctcttagttcacatctgtggtcagtctgggcttaatggcacccat
cctcccatttgctcatttggtctcagcagtgaatggaaaaagtgtctc
gtcctgacccctgcttcccttcctacttcctggaaatccacaggatg
ctgcatttgctcagcagatttaacagcccacttatcactcatggaagat
ccctcctcctgcttgactccgccctctctcctctgccgctttcaata
agaggcagagacagcagccagaggaaccgagaggctgagactaa

```
tcccacacctcccctgaacctgaaacataaaatgaatgcaattgttgt
tgttaacttgtttattgcagcttataatggttacaaataaagcaatagc
atcacaaatttcacaaataaagcattttttcactgcattctagttgtg
gtttgtccaaactcatcaatgtatcttaacgcgtcatatgggatccccg
gagcttgggctgcaggtcgagggacctaataacttcgtatagcatacat
tatacgaagttatattaaggggttccggatcgatccccatcaagcttcga
attcatggcttcgtaccccggccatcaacacgcgtctgcgttcgaccag
gctgcgcgttctcgcggccatagcaaccgacgtacggcgttgcgccctc
gccggcagcaagaagccacggaagtccgcccggagcagaaaatgcccac
gctactgcgggtttatatagacggtccccacgggatggggaaaaccacc
accacgcaactgctggtggccctgggttcgcgcgacgatatcgtctacg
tacccgagccgatgacttactggcgggtgctggggcttccgagacaat
cgcgaacatctacaccacacaacaccgcctcgaccagggtgagatatcg
gccggggacgcggcggtggtaatgacaagcgcccagataacaatgggca
tgccttatgccgtgaccgacgccgttctggctcctcatatcggggggga
ggctgggagctcacatgccccgccccggccctcaccctcatcttcgac
cgccatccatcgccgcctcctgtgctacccggccgcgcggtaccta
tgggcagcatgaccccaggccgtgctggcgttcgtggccctcatccc
gccgaccttgcccggcaccaacatcgtgcttggggcccttccggaggac
agacacatcgaccgcctggccaaacgccagcgccccggcgagcggctgg
acctggctatgctggctgcgattcgccgcgtttacgggctacttgccaa
tacggtgcggtatctgcagtgcggcgggtcgtggcgggaggactgggga
cagctttcggggacggccgtgccgccccagggtgccgagccccagagca
acgcgggcccacgaccccatatcggggacacgttatttaccctgtttcg
ggcccccgagttgctggccccaacggcgacctgtataacgtgtttgcc
tgggccttggacgtcttggccaaacgcctccgttccatgcacgtcttta
tcctggattacgaccaatcgcccgccggctgccgggacgccctgctgca
acttacctccgggatggtccagacccacgtcaccaccccggctccata
ccgacgatatgcgacctggcgcgcacgtttgcccgggagatgggggagg
ctaacggatccaccggatctagataactgatcataatcagccataccac
atttgtagaggttttacttgctttaaaaaacctcccacacctcccctg
aacctgaaacataaaatgaatgcaattgttgttgttaacttgtttattg
cagcttataatggttacaaataaagcaatagcatcacaaatttcacaaa
taaagcattttttcactgcattctagttgtggtttgtccaaactcatc
aatgtatcttaacgcgt
```

TRANSGENIC ANIMAL WITH MONOCYTE CHEMOTACTIC PROTEIN 1 PROMOTER

FIELD OF THE INVENTION

The preset invention features a transgenic animal which expresses one or more reporter genes under the control of a monocyte chemotactic protein 1 (MCP-1) promoter, and applications thereof.

BACKGROUND OF THE INVENTION

Inflammation is a local or systemic protective response to the injury or infection of cells or tissues. However, inflammation may lead to a large number of diseases due to an imbalance of inflammatory cytokines and by the interaction between effector cells. Main inflammatory diseases include: rhinitis and sinusitis such as infectious rhinitis, allergic rhinitis, chronic rhinitis, acute sinusitis and chronic sinusitis; pneumonia such as bacterial pneumonia, bronchial pneumonia, lobar pneumonia, Legionella pneumonia and viral pneumonia; otitis media such as acute purulent otitis media and chronic purulent otitis media; acute or chronic gastritis; enteritis such as infectious enterocolitis, Crohn's disease, idiopathic ulcerative colitis and pseudomembranous colitis; arthritis such as septic arthritis, tuberculous arthritis, degenerative arthritis and rheumatoid arthritis; and diabetic ocular disease.

MCP-1, also called chemokine (C-C motif) ligand 2 (CCL2), is a small cytokine belonging to the CC chemokine family. MCP-1 recruits monocytes and subset of lymphocytes (*Mol Med Today* (1996) 2: 198-204; *J Leukoc Biol* (1999) 65: 482-491). In previous studies, a high level of MCP-1 was detected in the branchoalveolar lavage fluids (BALF) and serum of patients with pulmonary sarcoidosis (*Internal Med* (1997) 36: 856-860; *Clin Exp Immunol* (1998) 111:604-610; *Eur Res J* (2002) 20:1206-1212; *Res Med* (2004) 98: 945-951), and it was suggested that MCP-1 served as an important mediator that dictated the granuloma progression. MCP-1 is also known to play an important role in the pathogenesis of many diseases such as asthma, interstitial lung diseases, and tumors. However, most studies are performed in in vitro experiments.

It is therefore desired to develop an animal model to study MCP-1 expression in vivo and further to screen for an agent that regulates MCP-1 expression or an agent that treats an inflammation disorder especially that where MCP-1 plays a key role.

BRIEF SUMMARY OF THE INVENTION

In one aspect, the invention provides a transgenic animal, which comprises in its genome a recombinant nucleic acid molecule comprising a polynucleotide encoding one or more reporter proteins, and a monocyte chemotactic protein-1 (MCP-1) promoter, wherein the one or more reporter proteins are expressed under the control of the MCP-1 promoter. In particular, the one or more reporter proteins are selected from the group consisting of at reporter protein detectable by fluorescent imaging, a reporter protein detectable by bioluminescence imaging, a reporter protein detectable by nuclear imaging, and any combination thereof. In one example of the invention, the reporter protein is enhanced green fluorescent protein (EGFP). In another example of the invention, the reporter protein is a fusion protein of EGFP, luciferase and herpes simplex virus type 1 thymidine kinase (HSV1-TK).

In another aspect, the invention provides a method for monitoring endogenous expression of MCP-1 in vivo comprising:
(a) providing a transgenic animal, which comprises in its genome a recombinant nucleic acid molecule comprising a polynucleotide encoding one or more reporter proteins, and a monocyte chemotactic protein-1 (MCP-1) promoter, wherein the one or more reporter proteins are expressed under the control of the MCP-1 promoter, and
(b) detecting in the transgenic animal the presence or level of the one or more reporter proteins as an indicator for the expression of the endogenous MCP-1.

In one embodiment of the invention, the method is useful for determining whether a candidate agent can regulate the expression of MCP-1 in a mammal; wherein the candidate agent is an inhibitor of the expression of MCP-1 if the level of the one or more reporter proteins is reduced after the administration with the candidate agent; and the candidate agent is an inducer of the expression of the MCP-1 if the level of the one or more reporter proteins is increased after the administration of the candidate agent.

In another embodiment of the invention, the method is useful for determining whether a candidate agent is anti-inflammatory agent; wherein the candidate agent is an anti-inflammatory agent if the level of the one or more reporter proteins is reduced after the administration with the candidate agent.

The various embodiments of the present invention are described in details below. Other characteristics of the present invention will be clearly presented by the following detailed descriptions and drawings about the various embodiments and claims.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings:

FIG. 4 shows the sequence of the nucleotide fragment composed of the MCP-1 promoter, the EGFP coding sequence and poly A sequence contained in the MCP-1-EGFP transgenic vector(SEQ ID NO: 2).

DETAILED DESCRIPTION OF THE INVENTION

The present invention features a novel transgenic animal characterized by a recombinant nucleic acid molecule carrying a polynucleotide encoding one or more reporter proteins, and a MCP-1 promoter, wherein the one or more reporter proteins are expressed under the control of the MCP-1 promoter. The transgenic animal can be used as an animal model to monitor MCP-1 expression in vivo based on the signal produced by the reporter protein(s) and specifically to screen for an agent that regulates MCP-1 expression and thus is effective as anti-inflammatory agent, particularly for an inflammation in association with MCP-1.

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

As used herein, the term "polynucleotide", "nucleic acid" or "nucleic acid molecule" refers to a polymer composed of nucleotide units, including naturally occurring nucleic acids, such as deoxyribonucleic acid ("DNA") and ribonucleic acid ("RNA") as well as nucleic acid analogs including those which have non-naturally occurring nucleotides. Polynucleotide can be synthesized, for example, using an automated DNA synthesizer. The term "nucleic acid" or "nucleic acid molecule" typically refers to a large polynucleotide. It will be understood that when a nucleic acid fragment is represented by a DNA sequence (i.e., A, T, G, C), this also includes an RNA sequence (i.e., A, U, G, C) in which "U" replaces "T."

As used herein, the term "recombinant" refers to a polynucleotide, nucleic acid or nucleic acid molecule having sequences that are not naturally joined together. A recombinant nucleic acid molecule may be present in the form of a construct. The term "construct" as used herein may include one or more given nucleotide sequences of interest, and regulatory sequences for expression of the given nucleotide sequence(s), such as a promoter sequence. Constructs may be used for expressing the given nucleotide sequence or maintaining the given nucleotide sequence for replicating it, manipulating it or transferring it between different locations (e.g., between different organisms). Constructs can be introduced into a suitable host cell for the above mentioned purposes.

Examples of constructs include, but are not limited to, plasmids, cosmids, phages, YACs or PACs. Typically, in a construct, the given nucleotide sequence is operatively linked to the regulatory sequence such that when the constructs are introduced into a host cell, the given nucleotide sequence can be expressed in the host cell under the control of the regulatory sequence. The regulatory sequence may comprises, for example and without limitation, a promoter sequence, a start codon, a replication origin, enhancers, an operator sequence, a secretion signal sequence and other control sequence (e.g., Shine-Dalgano sequences and termination sequences).

As used herein, the term "encoding" refers to the inherent property of specific nucleotide sequences in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides to reflect the codon usage of any particular host organism in which the polypeptides are to be expressed. Therefore, unless otherwise specified, a "nucleotide sequence encoding an amino acid sequence" or the like includes all nucleotide sequences that are degenerate versions of each other and that encode the same amino acid sequence. Nucleotide sequences that encode proteins and RNA may include introns.

As used herein, the term "promoter" means a DNA sequence that regulates expression of a particular gene operatively linked to the promoter, which effects transcription of the particular gene in cells. Promoters contain specific DNA sequences (response elements) which provide binding sites for RNA polymerase and transcriptional factors for transcription to take place. Typically, promoters are located near the genes they regulate on the same strand and upstream (towards the 5' region of the sense strand). Accordingly, as used herein, a "MCP-1 promoter" means a promoter of the gene, MCP-1. The sequence of a MCP-1 promoter is well known in this art, see for example, in Biochem. Biophys. Res. Commun. 169 (1990), pp. 346-351.

As used herein, a reporter protein is any protein that can be specifically detected when expressed, for example, via its color or enzyme activity. Reporter proteins are useful for assessing the activity of regulatory sequences responsible for expression of the reporter proteins such as promoter sequences. For example, operatively linking a nucleotide sequence encoding a reporter protein to a naturally occurring promoter sequence allows one to study the activation of the promoter sequence in response to different stimuli in vivo. In the invention, the reporter protein serves as a marker to show the activation of the promoter sequence. According to the invention, many reporter proteins known in the art may be used, including but not limited to beta-galactosidase, luciferase, and alkaline phosphatase that produce specific detectable products. The fluorescent reporter proteins includes, for example, green fluorescent protein (GFP), cyan fluorescent protein (CFP), red fluorescent protein (RFP) and yellow fluorescent protein (YFP) as well as modified forms thereof e.g. enhanced GFP (EGFP), enhanced CFP (ECFP), enhanced RFP (ERFP), and enhanced YEP (EYEP). In one example of the invention, GFP was used and fluorescence could be observed upon exposure to ultraviolet light without addition of a substrate. In addition, nuclear imaging is a method of producing images by detecting radiation from different parts of the body after a radioactive tracer material is administered; such images are recorded on a computer film for analysis by using such as γ-camera, SPECT, or positron emission tomography (PET). Some more reporter proteins detectable by noninvasive nuclear imaging may be used in the invention, such as herpes simplex virus type 1 thymidine kinase (HSV1-TK), norepinephrine transporter (NET), sodium iodine symporter (NIS). In the examples of the invention, radioactive tracer materials such as radiolabeled fialuridine (FIAU), 2'-fluoro-5-ethylarabinosyluracil (FEAU), 3-hydroxymethylbutyl)guanine (FHBG), and penciclovir (PCV) can be used for HSV1-TK, labeled iodide and pertechnetate can be used for NIS, and labeled metaiodobenzylguanidine (MIBG) can be used for NET.

As used herein, the term "transgenic animal" means an animal which carries a foreign genetic material, also called a transgene, which has been deliberately inserted into its genome. The transgene may be constructed using recombinant DNA methodology. Typical examples of transgenic animals are rodents, e.g. mice or rats. Generation of transgenic animals may be carried out by a number of conventional methods such as those described in Hogan et al., "Manipulating the Mouse Embryo", Cold Spring Harbor Laboratory Press, 1986; and Kraemer et al., "Genetic Manipulation of the Early Mammalian Embryo", Cold Spring harbor Laboratory Press, 1985.

In one aspect, the present invention provides a transgenic animal which comprises in its genome a recombinant nucleic acid molecule comprising a polynucleotide encoding one or more reporter proteins, and a monocyte chemotactic protein-1 (MCP-1) promoter, wherein the one or more reporter proteins are expressed under the control of the MCP-1 promoter. In particular, the polynucleotide is operatively linked to the MCP-1 promoter. According to the invention, the animal is a non-human mammal, including but not limited to primates, ungulates, canines, felines. In one example of the invention, the animal is a mouse.

According to the invention, the MCP-1 promoter may be derived from a human or non-human mammal. Non-human mammals include, but are not limited to, primates, ungulates, canines, felines, and rodents. In one embodiment of the invention, the MCP promoter has the nucleotide sequence of SEQ ID NO: 1.

According to the invention, the polynucleotide may encode one or more reporter proteins which are selected from those known in the art or any combination thereof. Specifically, the one or more reporter proteins according to the invention are selected from the group consisting of a reporter protein detectable by fluorescent imaging, a reporter protein detectable by bioluminescence imaging, a reporter protein detectable by nuclear imaging, and any combination thereof. Typically, the reporter protein detectable by fluorescent imaging may be GFP, CFP, RFP or YFP; the reporter protein detectable by bioluminescence imaging may be luciferase (Firefly luciferase or Rennila luciferase); and the reporter protein detectable by nuclear imaging may be HSV1-TK, NIS or NET.

In one embodiment of the invention, the polynucleotide encodes single reporter protein which is a reporter protein detectable by fluorescent imaging, a reporter protein detectable by bioluminescence imaging, or a reporter protein detectable by nuclear imaging. In one example of the invention, the reporter protein is EGFP, which is expressed under the control of a MCP-1 promoter. In one specific example, the recombinant nucleic acid molecule comprises the nucleotide sequence of SEQ ID NO: 2 which is composed of an EGFP coding sequence operatively linked to the nucleotide sequence of SEQ ID NO: 1 (i.e., the MCP-1 promoter) and followed by a poly A sequence.

In another embodiment of the invention, the polynucleotide encodes a fusion protein of two or more reporter proteins, selected from the group consisting of a reporter protein detectable by fluorescent imaging, a reporter protein detectable by bioluminescence imaging, and a reporter protein detectable by nuclear imaging. In one example of the invention, to provide one transgenic animal that can be detected by different manners, the polynucleotide encoding a fusion protein of a reporter proteins detectable by fluorescent imaging, a reporter protein detectable by bioluminescence imaging, and a reporter protein detectable by nuclear imaging is used. Particularly, the polynucleotide encoding a fusion protein of EGFP, luciferase, and HSV1-TK. Specifically, the recombinant nucleic acid molecule comprises in-frame coding sequences of said three reporter proteins operatively linked to the nucleotide sequence of SEQ ID NO: 1.

It is understood that one may obtain the nucleotide sequences of one or more reporter proteins and a MCP-1 promoter based on commonly used or known technologies and knowledge to prepare the recombinant nucleic acid molecule according to the invention. Any genetic engineering techniques may be used to prepare the recombinant polynucleotide according to the invention, such as polynucleotide synthesis, polymerase chain reaction (PCR), cloning, nucleic acid purification, vector construction, and enzymatic treatment and sequencing of vectors and nucleic acid fragments, see for example Sambrook et al., Molecular Cloning: A Laboratory Manual, $2^{nd}$ ed., Cold Spring Harbor Laboratory Press (1989), and Frederick M. A. et al., Current Protocols in Molecular Biology, John Wiley & Sons, Inc. (2001). Details for the preparation of the recombinant polynucleotide of the invention are described in the examples below.

It is also understood that anyone skilled in the art can produce a transgenic animal of the invention in light of the teachings as provided herein by using known standard techniques such as those described above. For example, the recombinant polynucleotide of the invention is directly injected into the male pronucleus of the fertilized egg, and the injected eggs are then re-transferred into the uteri of pseudopregnant recipient mothers and the resulting offspring will have one or several copies of the transgene integrated into their genomes. These "founder" animals are then bred to establish transgenic lines and to back-cross into the genetic background of choice. The transgenic animals may be identified, for example, by detecting the presence of the transgene by PCR with specific primers, or by southern blotting, preferably of tail DNA, with a specific probe.

According to the invention, the expression of the one or more reporter proteins driven by a MCP-1 promoter mimics the endogenous MCP-1 expression in vivo. As demonstrated in the following examples, the expression of EGFP driven by a human MCP-1 promoter was correlated to the endogenous MCP-1 expression in the transgenic animal of the invention. Therefore, the transgenic animal of the invention may be used to monitor endogenous expression of MCP-1 in vivo, which facilitates better understanding of the role of MCP-1 in various diseases. Also, the transgenic animal of the invention may be used to identify an agent that regulates expression of MCP-1 or an agent that treats an inflammatory disorder, especially those where MCP-1 plays a vital role Accordingly, the present invention further provides a method for monitoring endogenous expression of MCP-1 in vivo comprising:
(a) providing a transgenic animal, which comprises in its genome a recombinant nucleic acid molecule comprising a polynucleotide encoding one or more reporter proteins, and a monocyte chemotactic protein-1 (MCP-1) promoter, wherein the one or more reporter proteins are expressed under the control of the MCP-1 promoter, and
(b) detecting in the transgenic animal the presence or level of the one or more reporter proteins as an indicator for the expression of the endogenous MCP-1.

It is understood that detection of the reporter protein can be accomplished through various methods known in this art, including, but not limited to colorimetric, fluorimetric or luminometric assays or nuclear imaging depending on the natural of the reporter genes as used.

In one example of the invention, the polynucleotide encodes single reporter protein, such as EGFP; and in Step (b) fluorescent imaging is used to detect the EGFP. Specifically, in Step (b), freshly dissected tissues from the transgenic animal are obtained and observed under a fluorenscence stereo microscope with a GFP filter for detection of the expression of the reporter protein, which is indicative of endogenous MCP-1 expression in the transgenic animal.

In another example of the invention, the polynucleotide encodes a fusion protein of three reporter proteins, such as the fusion protein of EGFP, luciferase, and HSV1-TK; and in Step (b) fluorescent imaging is used to detect the enhanced GFP; bioluminescence imaging is used to detect the luciferase; and/or nuclear imaging is used to detect HSV1-TK. In one example of the invention, in Step (b), to conduct nuclear imaging, a radioactive tracer material is administered and the image thus produced is detected using γ-camera, SPECT, or positron emission tomography (PET), for example, in a noninvasive manner. It is understood that such multimodality imaging system allows efficient and flexible analysis of the gene expression in cells or tissues of living animals.

In one embodiment of the invention, the method is useful for determining whether a candidate agent can regulate the expression of MCP-1 in a mammal; wherein the candidate agent is an inhibitor of the expression of MCP-1 if the level of the reporter protein is reduced after the administration with the candidate agent; and the candidate agent is an inducer of the expression of the MCP-1 if the level of the reporter protein is increased after the administration of the candidate agent.

In another embodiment of the invention, the method is useful for determining whether a candidate agent is an anti-inflammatory agent; wherein the candidate agent is an anti-inflammatory agent if the level of the reporter protein is reduced after the administration with the candidate agent.

The term "anti-inflammatory agent" used herein means an agent having a characteristic to suppress, reduce, eliminate, treat, or ameliorate an inflammatory response caused by an inflammatory disorder. In particular, the inflammatory disorder is in association with MCP-1, including but not limited to arthritis, asthma, atherosclerosis, neurodegenerative, obesity-induced adipose tissue inflammation, insulin resistance, nephritis, lupus, autoimmune lymphoproliferative, tumor oncolytic processes, pulmonary granuloma, and the autoimmune diseases. In one example of the invention, the inflammatory disorder is an inflammatory disorder of lung, such as a pulmonary granulomatous inflammation.

The present invention will now be described more specifically with reference to the following embodiments, which are provided for the purpose of demonstration rather than limitation.

Example 1

Construction of the MCP-1-EGFP Transgenic Vector

Figure 1:
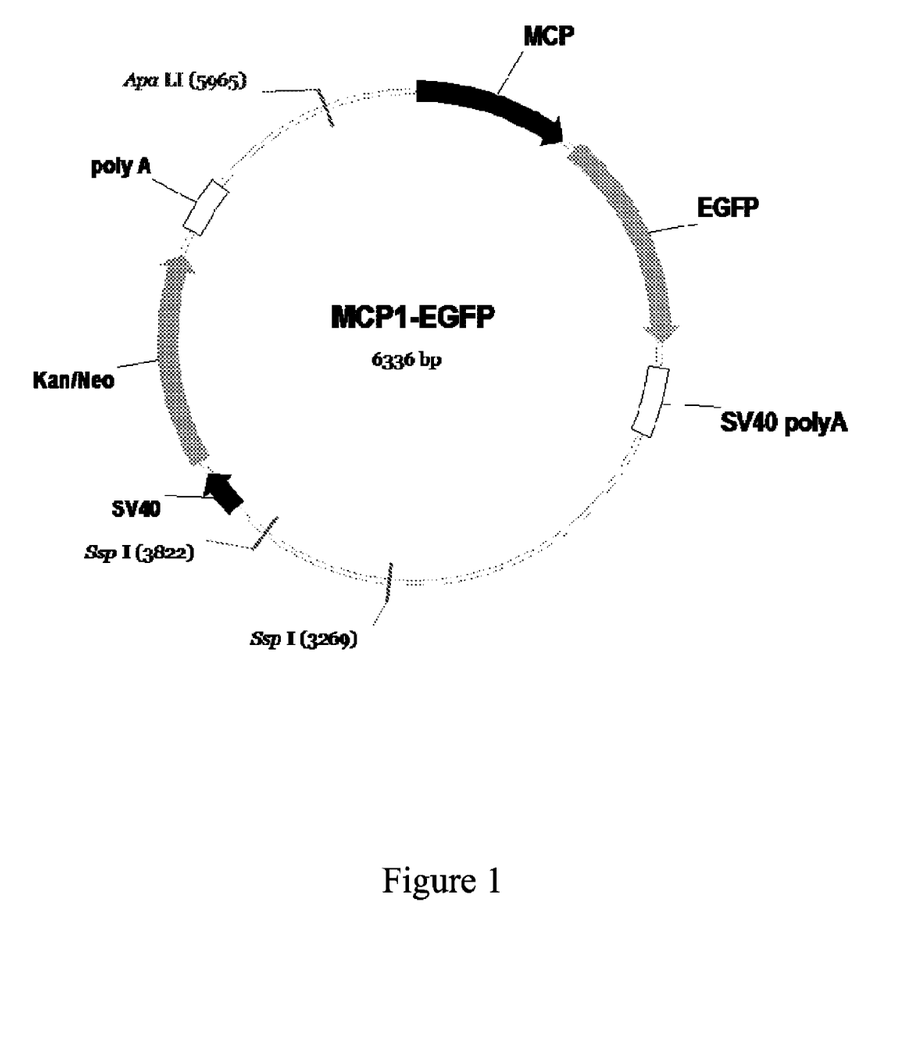
FIG. 1 shows the structural map of the MCP-1-EGFP transgenic vector obtained in Example 1.
Figure 2:
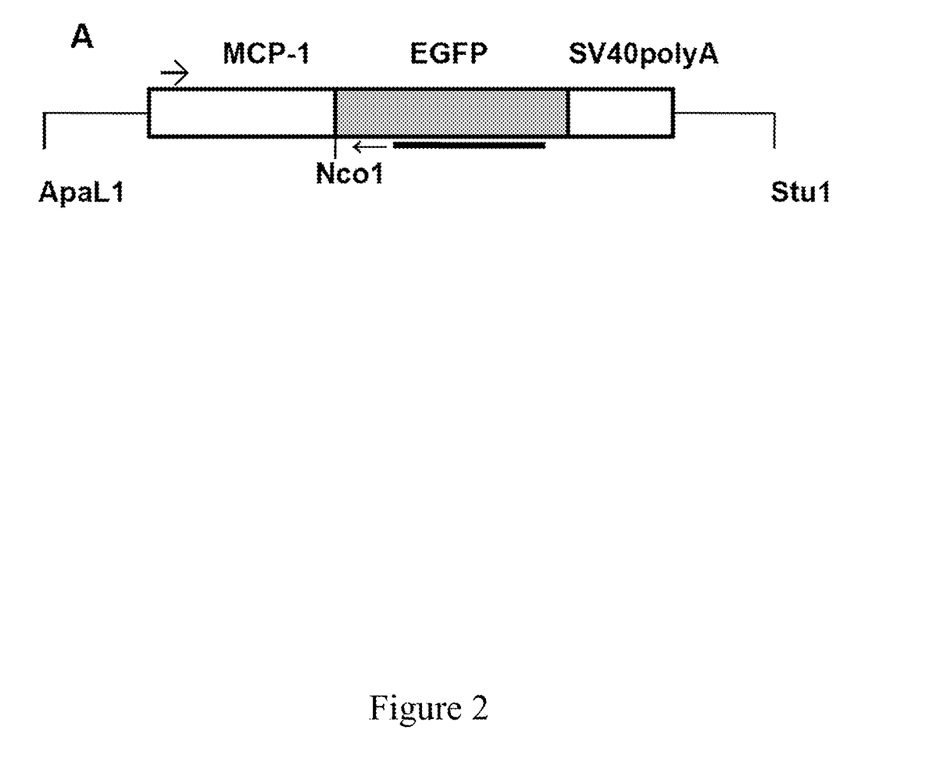
FIG. 2 shows the position of the MCP-1 immediate early promoter and that of the EGFP coding sequence in the MCP-1-EGFP transgenic vector; wherein arrows indicate the binding locations of the primers for the genotyping PCR conducted in Example 2; and the underlined region indicates the location of the probe for Southern blot analysis performed in Example 2.
Figure 3:
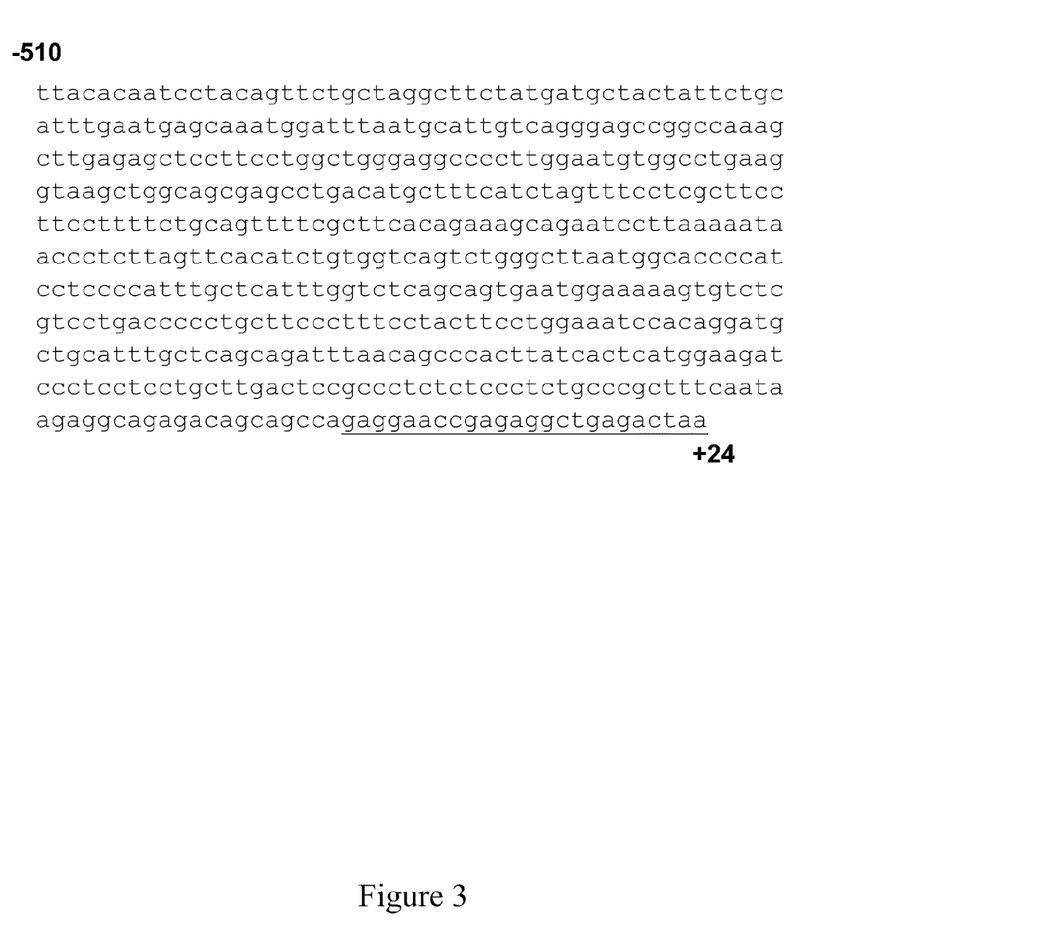
FIG. 3 shows the sequence of the MCP-1 promoter (SEQ ID NO: 1) in the MCP-1-EGFP transgenic vector.

The human immediate early promoter of 534 bp (SEQ ID NO: 1) was acquired by Xho1 and BamH1 digestion of MCP1-540-Luc vector as described in *Biochem. Biophys. Res. Commun.* 169 (1990), pp. 346-351. The product was then ligated before the EGFP coding sequence and the SV 40 polyadenylation sequence in a pEGFP-C2 vector (Clonetech, USA) to produce a transgenic vector encoding EGFP under the control of the MCP-1 promoter, called the MCP-1-EGFP Transgenic Vector. FIG. 1 shows the structural map of the MCP-1-EGFP transgenic vector thus obtained. FIG. 2 shows the position of the MCP-1 immediate early promoter in the MCP-1-EGFP transgenic vector.

In addition, a DNA sequencing analysis was conducted, revealing that the MCP-1-EGFP transgenic vector comprises the nucleotide sequence of SEQ ID NO: 2 composed of the MCP-1 promoter, the EGFP coding sequence, and the polyA sequence.

Example 2

Generation of MCP-1-EGFP Transgenic Mice

The MCP-1-EGFP transgenic vector obtained in Example 1 was used to generate MCP-1-EGFP transgenic mice. Briefly, FVB/NarL mice (MHC type $2^q$) were provided for preparing the transgenic mice. The purified MCP1-EGFP-PolyA fragment was excised from the vector by digestion with ApaL1 and Ssp1 and injected into the FVB mouse embryos, according to the procedure described in Nagy et al., (2003) Manipulating the mouse embryo: A laboratory manual, 3rd edn. Cold Spring Harbor Laboratory, Cold Spring Harbor, N.Y., at the Level Transgenic Center (Taipei, Taiwan). Transgenic mice were generated and housed under standard specific pathogen free facility conditions. All studies concerning the use of mice were conducted in accord with the rules established by the IACUC at the Institute of National Health Research Institutes, Taiwan.

The transgenic mice thus obtained were screened by a Southern blot analysis to confirm the integration of the MCP-1-EGFP transgene. Nco1 was used to digest the mouse tail DNA samples followed by electrophoresis with 0.8% agarose gel. The probe used for Southern blotting is a 752 bp fragment (SEQ ID NO: 3) of EGFP coding sequence.

Figure 5:
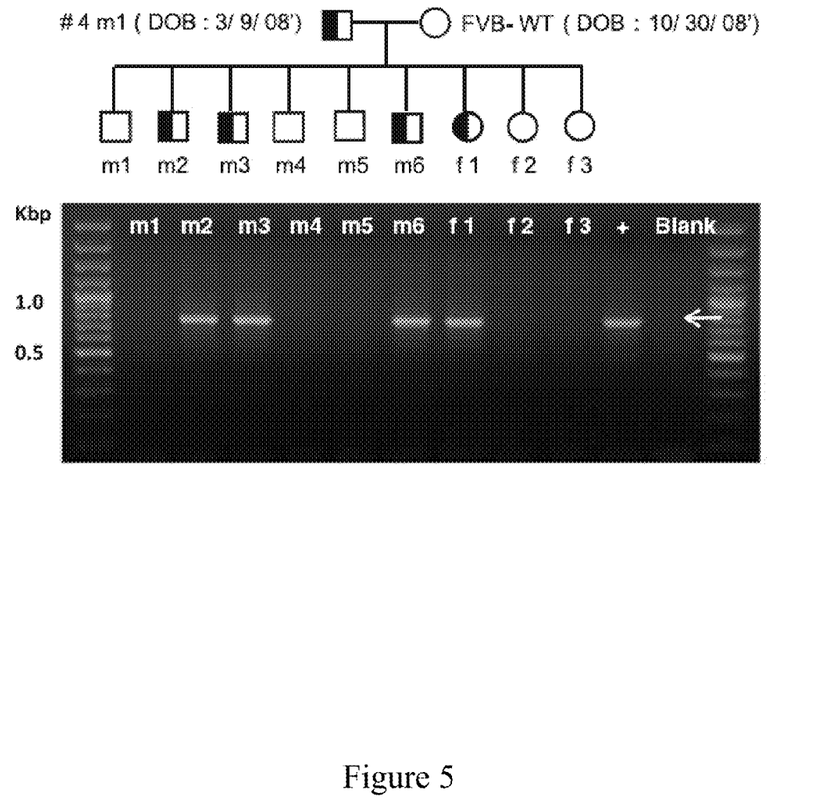
FIG. 5 shows the results of the representative genotyping PCR amplifying the transgenic fragment (marked by the arrow as shown in FIG. 2) from the tail DNA samples.

Of the mice tested, the founder line No. 4 (born on Sep. 3, 2008) was confirmed to carry single or low copies of transgene, and only mice from the founder line No. 4 was used in the following studies. In this regard, a genotyping PCR method was used to screen for transgene positive litters. In a representative example, the primers used in the genotyping PCR method were as follows: ACCGAGCTCGGATCCAC-TAGTAACG (as the sense primer located in human MCP1 promoter; SEQ ID NO: 4) and CTCACCATGGTGGCGAC-CGG (as the reverse primer located in EGFP; SEQ ID NO: 5), and as shown in FIG. 5, littermate m2, m3, m6, and f1 carried the transgene from the founder line No. 4.

Example 3

Induction of Inflammation in the Transgenic Mouse and Relevant Analyses Thereof 1. Induction of Foreign Body Pulmonary Granulomatous Inflammation by SDX Foreign body pulmonary granulomatous inflammation was introduced in 8 to 10 weeks old MCP-1-EGFP transgenic mice by intratracheally (i.t.) instillation of Sephadex (SDX) G-50 superfine beads (Amersham Biosciences) using a modified protocol (*Am J Pathol* (1995) 147:1001-1015; *J Immunol* (2002) 168:3004-3016). Briefly, SDX beads were washed several times with phosphate buffered saline (PBS, pH 7.4), autoclaved, and resuspended in PBS at a concentration of $2.0 \times 10^5$ beads/ml. Fifty µl of SDX-PBS solution was then i.t. instilled into the lung of anesthetized mice. Shame control mice were instilled with 50 µl of PBS alone. Treated mice were sacrificed at the end of day 1, day 3, and day 5 after SDX or PBS instillation, and untreated mice were sacrificed as a naive control.

All the grouped data were statistically evaluated with SPSS/7.5 software. Hypothesis testing methods included one-way analysis of variance (ANOVA) followed by least significant difference (LSD) test. $P < 0.05$ was considered as statistically significant. All results were expressed as mean±SD. for 4 to 5 animals in each group.

2. Leukocyte Counts in BALF

BALF collection was performed as previously described (*Clin Immunol Immunopathol* (1994) 73:312-329) by gently instilling 6 ml of sterile PBS in 1 ml aliquots into the lung via a tracheal catheter followed by withdrawal, and approximately eighty percent of the instilled fluid was retrieved at the end of the each lavage procedure. After removing the red blood cells, the number of cells in lavage fluid was counted using a haemocytometer. Cytological slides were prepared by cytospin and stained with modified Wright-Giemsa stain (Sigma) to determine the total number of individual cell type.

Figure 6:
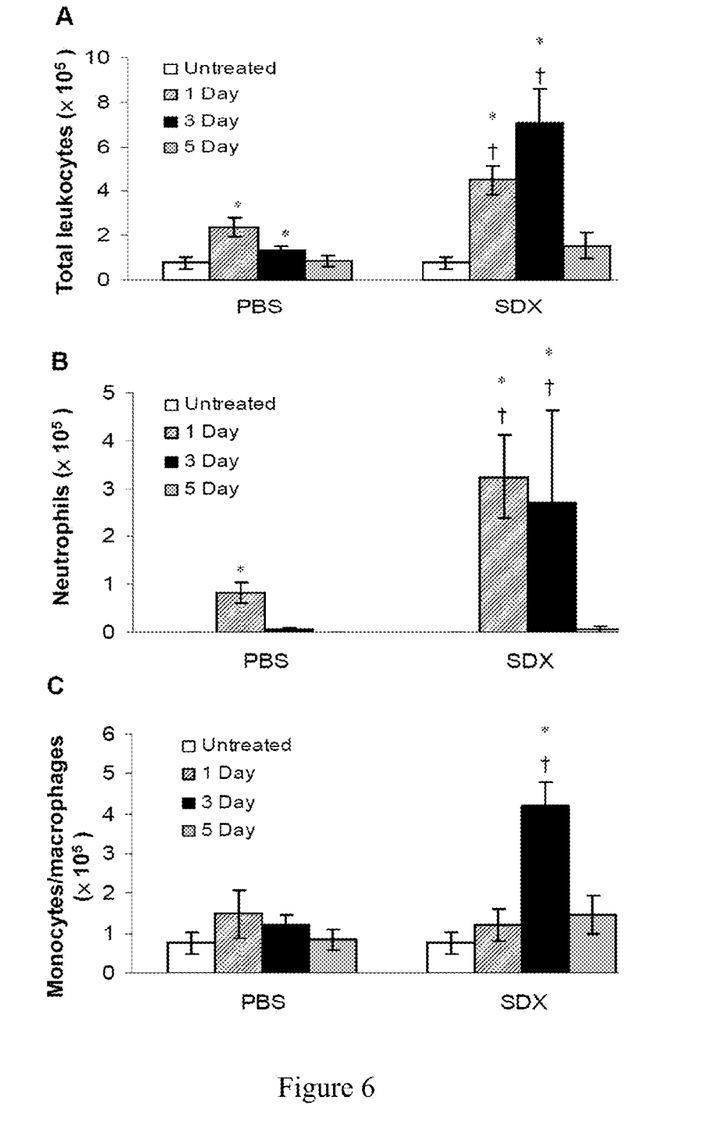
FIG. 6 shows the different cell types (A: total leukocytes; B: neutrophils; and C: macrophages) presented in BALF of different experimental groups; wherein the results are expressed as the mean±SD of 4 to 5 animals. * P<0.05, compared with untreated groups; † P<0.05, compared with PBS treated group.

The results show that SDX instillation led to a massive increase in total leukocytes counts in BALF recovered after 1 and 3 days as compared with untreated or PBS injected controls. At the end of 5 days, no significant difference in total cell counts was observed in PBS or SDX treated groups (FIG. 6A). Noticeably, BALF of untreated mice contained only mononuclear cells but no granulocytes (FIGS. 6B and 6C). PBS instillation induced a significant increase in neutrophils number only at the end of day 1, and returned to normal later. Upon SDX instillation, neutrophils number was maximally increased at day 1, remained high at day 3, and nearly absent after day 5 (FIG. 6B). In contrast, an increase in monocytes/macrophages numbers was observed at day 1, reaching maximum level at day 3, and declining thereafter (FIG. 6C).

3. Histological Observations

Lungs were fixed in 10% formalin followed by paraffin-embedding. Thin sections (4 µm) were stained with hematoxylin and eosin (H&E) and examined for histological evaluation. For immunohistochemical analyses, antigens were retrieved by sodium citrate method and the endogenous peroxidase activity was quenched by preincubation in 3% $H_2O_2$ solution.

According to the results, histological examinations on the lung of SDX-treated mice revealed significant inflammatory cells infiltration but not in lungs of untreated or PBS treated mice (data not shown). Granulomas with neutrophils infiltration were evident by day 1, developing in size by day 3, and then gradually decreased. At the end of day 3, dense neutrophils but few macrophages appeared around the beads, whereas on day 5, SDX beads were surrounded by dense mononuclear cell infiltrates but few neutrophils at the periphery of the granuloma.

4. Ex-vivo Green Fluorescence Imaging in Lung Tissue and Bronchoalveolar Lavage Fluid (BALF) Cells Freshly dissected lung tissues were obtained from the treated and untreated mice and observed under fluorescence stereo microscope (Olympus SZX10) with GFP filter (excitation 480 nm, emission 510 nm). In addition, at the end of each experimental period, mice were slightly anesthetized, the diaphragm and rib cage were cut open, and the heart and lungs were exposed. Murine blood was removed by intracradiac aspiration, the trachea was isolated, and a narrow blunt edged catheter (20 G) was inserted through a small incision and tied in a place. 6 ml of sterile PBS at room temperature was infused into the lungs in 1 ml aliquots using a tuberculin syringe and a gentle suction was applied after each infusion to aspirate the fluid whose volume was then recorded. Approximately eighty percent of the instilled fluid was retrieved at the end of the each lavage procedure. The collected cells were washed by centrifugation (400 g×10 minutes); twice or three times in RPMI 1640 containing FCS 10%, gentamycin (50 µg/ml), and glutamine (2 mM); and resuspended in medium by gentle agitation. Contaminating red blood cells were lysed with Tris buffered ammonium chloride and cell counts were determined using hemocytometer. Cytocentrifuge preparations (1200 rpm×2 minutes) of BALF cells (0.5 to $1.0 \times 10^5$ cells/slide) were air dried and stained with modified Wright-Giemsa stain (Sigma) to determine the total number of individual cell types. For the detection of florescence, cell collections were performed rapidly and observed using fluorescent microscope (Olympus BX51).

According to the results (data not shown), an increase of fluorescence was found in the lung of the SDX treated MCP-1 EGFP mice, and an increase in the number of green fluorescent cells and the intensity of green fluorescence was found in the BALF of the SDX treated mice compared to the PBS treated mice.

5. Lung MCP-1 and EGFP Gene Expression Study by qPCR and RT-PCR

Total cellular RNA was isolated from untreated mice lung and at various time points after PBS or SDX instillation using RNA isolation kit (Roche). RNA samples were treated with DNase 1 to eliminate genomic DNA contamination. Five µg of total RNA was subjected to the first strand cDNA synthesis using reverse transcription kit (Qiagen) and the product was used as templates for amplification in quantitative PCR (qPCR) using the SYBR green master mix (Applied Biosystems) and gene specific primers. The primer sets used in qPCR were primers for MCP-1 (GCCCCACTCACCTGCTGCTA (SEQ ID NO: 6); TTTACGGGTCAACTTCACATT CAA (SEQ ID NO: 7)), primers for EGFP (CTGCTGCCCGACAACCA (SEQ ID NO: 8); GAACTCCAGCAGGACCATGTG (SEQ ID NO: 9)), and primers for GAPDH (AGAATGGGAAGCTTGTCATC (SEQ ID NO: 10); GTAGACTCCACGACATACTC (SEQ ID NO: 11)) that was used as an internal control. Cycling conditions were 10 min at 95° C., followed by 45 cycles of a 15 s denaturation at 95° C., annealing at 60° C., and 15 s extension at 95° C. The mRNA level was quantified by: Cycle threshold ($\Delta Ct$)=Ct(MCP-1)−Ct(GAPDH).

In parallel, RT-PCR was also performed and the amplified PCR fragment was analyzed by 1.0% agarose gel. The primers used for RT-PCR are as follows: primers for MCP-1 (CTCACCTGCTGCTACTCATTC (SEQ ID NO: 12); GCTTGAGGTGGTTGTGGAAAA (SEQ ID NO: 13)); primers for EGFP (CCTACGGCGTGCAGTGCTTCAGC (SEQ ID NO: 14); TGCTCAGGTAGTGGTTGT (SEQ ID NO: 15)); primers for GAPDH (GTGGCAAAGTGGAGATTGT-TGCC (SEQ ID NO: 16); GATGATGACCCGTTTGGCTCC (SEQ ID NO: 17)).

Figure 7:
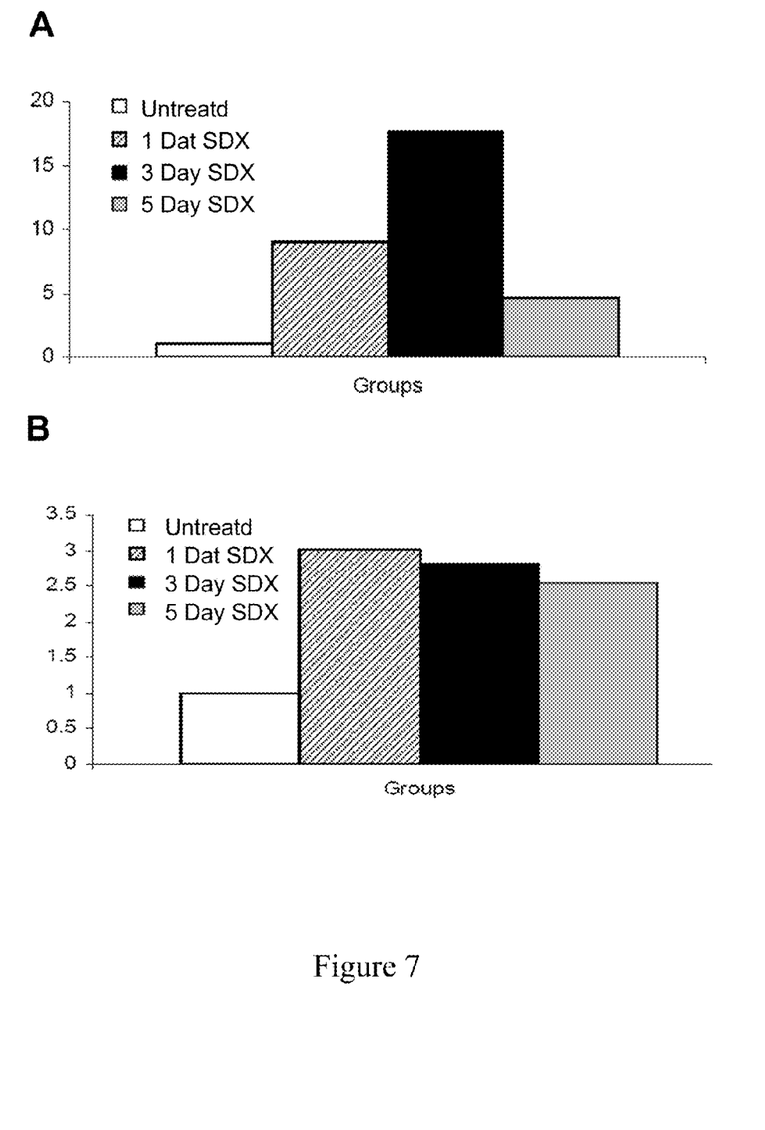
FIG. 7 shows the RT-PCR results revealing the increase of the mRNA levels of MCP-1 (A) and EGFP (B) at Days 1, 3 and 5 after SDX administration; wherein the expression of MCP-1 or EGFP was normalized to GAPDH and the fold of changes was obtained from two experiments.

FIG. 7 shows the RT-PCR results. In untreated MCP-1-EGFP mouse lung, there was detectable expression level of MCP-1 and EGFP transcripts. SDX instillation resulted in significant MCP-1 and EGFP induction at the end of day 1, day 3 and declined toward basal levels after day 5. The maximum of MCP-1 induction by SDX was approximately 18 folds after day 3 and rapidly declined afterwards, and the induction of EGFP was approximately 3 folds from day 1 through day 5. PBS instillation also induced MCP-1 and EGFP after day 1 but returned toward basal level after day 3. It should be noted that granuloma was not formed in PBS treated groups given the fact that PBS induced a transient MCP-1 expression.

6. MCP-1 and EGFP Protein Expression Study by ELISA and Western Blot

The protein in tissue homogenates was extracted by RIPA lysis buffer containing proteinase inhibitors (Upstate, CA) and the concentration was determined by Bradford assay (Bio-Rad, CA). Concentration of MCP-1 in lung tissue homogenates was determined by MCP-1 ELISA kit according to manufacturer's instructions (R&D Systems, Minneapolis, Minn.). The protein expression was subjected to 15% SDS-PAGE analysis followed by Western blotting using anti-EGFP (Abcam) and anti-β-actin (Chemicon), followed by detection with appropriate HRP conjugated secondary antibodies and ECL detection system.

Figure 8:
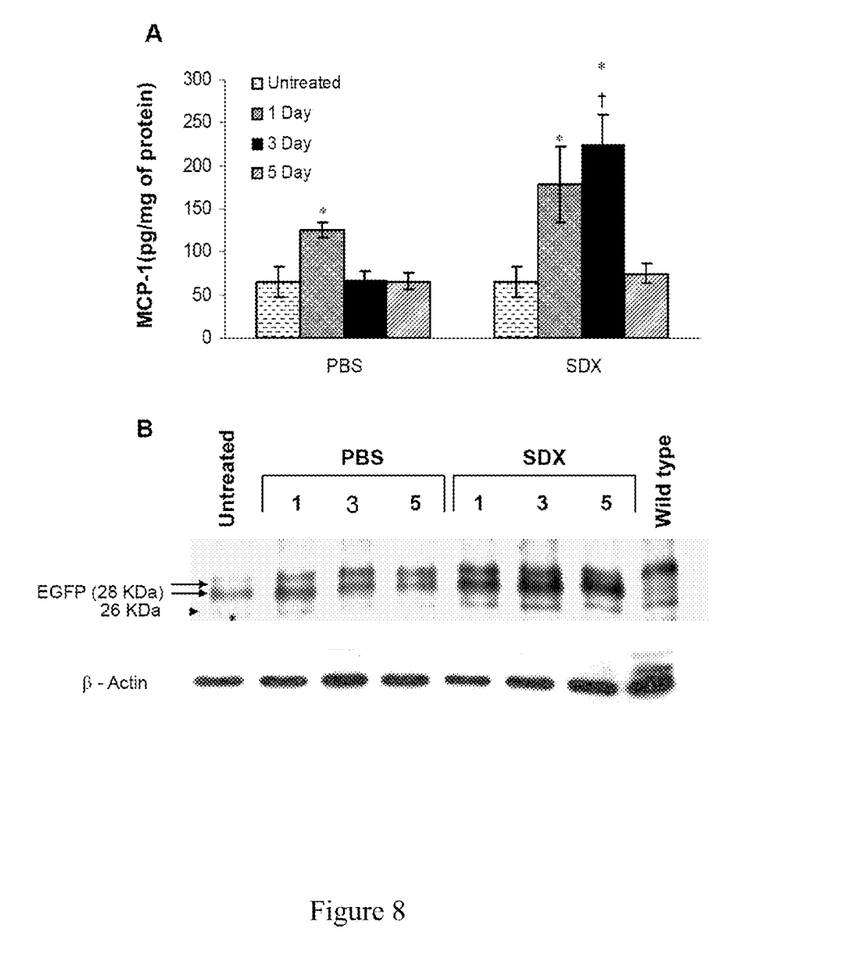
FIG. 8A shows the ELISA results of the MCP-1 protein expression induced by SDX in lung homogenates at Days 1, 3, and 5 after SDX administration; wherein the results are expressed as the mean±SD of 4 to 5 animals; the symbol "*" means P<0.05 compared with untreated groups; and the symbol "†" means P<0.05 compared with PBS treated group.
FIG. 8B shows the result of the Western blotting analysis revealing the increase of the expression level of EGFP protein induced by SDX at Days 1, 3, and 5 after SDX administration; wherein the two closely located bands of about 28 kDa are found to be the EGFP protein (arrows); a 26 kDa molecular weight marker is also shown (arrowhead); and β-actin was used as an internal standard.

As shown in FIG. 8A, the protein expression of MCP-1 is higher in SDS treated mice than that in PBS treated mice, and as shown in FIG. 6B, the protein expression of EGFP is higher in SDS treated mice than that in PBS treated mice. It is noted that there was a basal level of EGFP expression (FIG. 8B) appearing as two bands in Western blotting in untreated MCP-1-EGFP mouse lung. The upper band of doublets may represent an intermediate form of newly synthesized EGFP. Both bands were slightly increased by PBS instillation and strongly increased by SDX.

7. Immunohistochemical (IHC) Analysis of MCP-1 and EGFP in Lung

Lung sections were obtained and stained as described in Example 3.3. For detection of MCP-1 protein, the lung sections were blocked in 5% normal donkey serum and then incubated with goat anti-mouse CCL2/JE/MCP-1 (R&D Systems), HRP-labeled donkey anti-goat secondary antibody followed by color development with DAB kit (Vector Laboratories), counterstained with hematoxylin, and finally examined under light microscope. For detection of EGFP protein, the lung sections were blocked in 5% goat serum, incubated with rabbit polyclonal antibody to GFP (Abcam), followed by HRP-labeled goat anti-rabbit secondary antibody, color development with AEC kit (Vector Laboratories) and counterstained with hematoxylin.

According to the results (data not shown), positive staining for both MCP-1 and EGFP were rarely detected in untreated and PBS injected controls. However, in SDX treated lung, MCP-1 and EGFP expression was found not only in the cytoplasm of alveolar macrophages, macrophages around the SDX beads, but also in bronchiolar epithelial cells. The distribution pattern of EGFP positive staining is in agreement to that of MCP-1 staining, indicating colocalized MCP-1 and EGFP expression.

Example 4

Generation of Animal Model of LPS Induced Inflammation and Relevant Analyses Thereof To generate an animal model of LPS induced inflammation, the MCP-1-EGFP transgenic mice as obtained in Example 2 were treated with LPS (6 mg/kg; i.p.) for 24 hr. Wild-type mice and the MCP-1-EGFP transgenic mice without any treatment were provided as control groups for the following study.

Surface staining of Gr-1, a marker for granulocytes, and Mac-1, a marker for monocyte/macrophage, was conducted to differentiate the cells types in isolated bone marrow cells. Briefly, bone marrow cell suspensions were obtained by flushing tibias and femurs with PBS and the isolated cell suspensions were washed, followed by labeling with the mixture of antibodies: Mac-1 conjugated with phycoerythrin (PE) (Biolegend), biotinylated Gr-1 antibody, and streptavidin conjugated with PE-C7 secondary antibody (eBioscience) for cell surface staining According to the results (data not shown), the distribution of bone marrow Mac-1 (+) and Gr-1 (+) subpopulations was comparable between wild type and untreated MCP-1 control. After LPS treatment, there was a decrease of Gr-1 (+) and a concomitant increase of a unique subpopulation of Gr-1 (+) and Mac-1 (+) cells with high Mac-1 expression. This subpopulation exhibited a higher level of green fluorescence as detected by FACS analysis. This result indicates that bone marrow cells with increased Mac-1 expression by LPS also displayed a higher MCP-1 promoter activity resulting in a higher level of green fluorescence.

Given the above, by constructing a fluorescent MCP-1 reporter transgenic mouse, we were able to correlate EGFP reporter expression to the MCP-1 induction following lung granuloma inflammation. This MCP-1-EGFP mouse model will provide a valuable tool to monitor the activation of monocytes/macrophages and facilitate the studies on the roles of MCP-1 gene in various inflammatory diseases.

I claim:

1. A non-human transgenic animal, which comprises in its genome a recombinant nucleic acid molecule comprising a monocyte chemotactic protein-1 (MCP-1) promoter and a polynucleotide encoding an enhanced GFP (EGFP) expressed under the control of the MCP-1 promoter, wherein the recombinant nucleic acid molecule comprises the nucleotide sequence of SEQ ID NO: 2.

2. A method for monitoring endogenous expression of MCP-1 in vivo comprising:
   (a) providing a non-human transgenic animal, which comprises in its genome a recombinant nucleic acid molecule comprising a monocyte chemotactic protein-1 (MCP-1) promoter and a polynucleotide encoding an EGFP expressed under the control of the MCP-1 promoter, and
   (b) detecting in the transgenic animal the presence or level of the EGFP as an indicator for the expression of the endogenous MCP-1;
   wherein the recombinant nucleic acid molecule comprises the nucleotide sequence of SEQ ID NO: 2.

3. The method of claim 2, wherein fluorescent imaging is performed to detect the EGFP.

4. The transgenic animal of claim 1, wherein the transgenic animal is a mammal.

5. The transgenic animal of claim 4, wherein the transgenic mammal is a primate, ungulate, canine, or feline.

6. The transgenic animal of claim 4, wherein the mammal is a mouse.

7. The method of claim 2, wherein the transgenic animal is a mammal.

8. The method of claim 7, wherein the mammal is a primate, ungulate, canine, or feline.

9. The method of claim 7, wherein the mammal is a mouse.

* * * * *

SEQUENCE LISTING

<160> NUMBER OF SEQ ID NOS: 17

<210> SEQ ID NO 1
<211> LENGTH: 534
<212> TYPE: DNA
<213> ORGANISM: Homo sapiens
<220> FEATURE:
<222> LOCATION: (1)..(534)
<223> OTHER INFORMATION: MCP-1 promoter

<400> SEQUENCE: 1

```
ttacacaatc ctacagttct gctaggcttc tatgatgcta ctattctgca tttgaatgag      60
caaatggatt taatgcattg tcagggagcc ggccaaagct tgagagctcc ttcctggctg     120
ggaggcccct tggaatgtgg cctgaaggta agctggcagc gagcctgaca tgctttcatc     180
tagtttcctc gcttccttcc ttttctgcag ttttcgcttc acagaaagca gaatccttaa     240
aaataaccct cttagttcac atctgtggtc agtctgggct taatggcacc ccatcctccc     300
catttgctca tttggtctca gcagtgaatg gaaaaagtgt ctcgtcctga ccccctgctt     360 cccttttccta cttcctggaa atccacagga tgctgcattt gctcagcaga tttaacagcc     420
cacttatcac tcatggaaga tccctcctcc tgcttgactc cgccctctct ccctctgccc     480
gctttcaata agaggcagag acagcagcca gaggaaccga gaggctgaga ctaa           534
```

<210> SEQ ID NO 2
<211> LENGTH: 3251
<212> TYPE: DNA
<213> ORGANISM: Artificial Sequence
<220> FEATURE:
<223> OTHER INFORMATION: nucletide fragment in MCP-1-EGFP transgenic
      vector

<400> SEQUENCE: 2

```
tagttattag ggaggtaccg agctcggatc cactagtaac ggccgccagt gtgctggaat      60
tcggcttaca caatcctaca gttctgctag gcttctatga tgctactatt ctgcatttga     120
atgagcaaat ggatttaatg cattgtcagg gagccggcca agcttgaga gctccttcct      180 ggctgggagg cccttggaa tgtggcctga aggtaagctg gcagcgagcc tgacatgctt     240
tcatctagtt tcctcgcttc cttcctttc tgcagttttc gcttcacaga aagcagaatc     300
cttaaaaata accctcttag ttcacatctg tggtcagtct gggcttaatg gcaccccatc     360
ctccccattt gctcatttgg tctcagcagt gaatggaaaa agtgtctcgt cctgaccccc     420
tgcttccctt tcctacttcc tggaaatcca caggatgctg catttgctca gcagatttaa     480
cagcccactt atcactcatg gaagatccct cctcctgctt gactccgccc tctctccctc     540
tgcccgcttt caataagagg cagagacagc agccagagga accgagaggc tgagactaaa     600
gccgaattct gcagatatcc atcacactgg cggccgctcg agatctcgac tctagaggat     660
cagcttgggc tgcaggtcga gggacctaat aacttcgtat agcatacatt atacgaagtt     720
atattaaggg ttccggatct gctagcgcta ccggtcgcca ccatggtgag caagggcgag     780
gagctgttca ccggggtggt gcccatcctg gtcgagctgg acggcgacgt aaacggccac     840
aagttcagcg tgtccggcga gggcgagggc gatgccacct acggcaagct gaccctgaag     900
ttcatctgca ccaccggcaa gctgcccgtg ccctggccca cctcgtgac cacctgacc      960 tacggcgtgc agtgcttcag ccgctacccc gaccacatga agcagcacga cttcttcaag    1020
tccgccatgc ccgaaggcta cgtccaggag cgcaccatct tcttcaagga cgacggcaac    1080
tacaagaccc gcgccgaggt gaagttcgag ggcgacaccc tggtgaaccg catcgagctg    1140
aagggcatcg acttcaagga ggacggcaac atcctggggc acaagctgga gtacaactac    1200
aacagccaca acgtctatat catggccgac aagcagaaga cggcatcaa ggtgaacttc     1260 aagatccgcc acaacatcga ggacggcagc gtgcagctcg ccgaccacta ccagcagaac    1320 accccctcg gcgacggccc cgtgctgctg cccgacaacc actacctgag cacccagtcc    1380
gccctgagca agacccccaa cgagaagcgc gatcacatgg tcctgctgga gttcgtgacc    1440
gccgccggga tcactctcgg catggacgag ctgtacaagt ccgccggac tcagatccac    1500 cggatctaga taactgatca taatcagcca taccacattt gtagaggttt tacttgcttt    1560
```

-continued

```
aaaaaacctc ccacacctcc ccctgaacct gaaacataaa atgaatgcaa ttgttgttgt    1620
taacttgttt attgcagctt ataatggtta caaataaagc aatagcatca caaatttcac    1680
aaataaagca ttttttcac tgcattctag ttgtggtttg tccaaactca tcaatgtatc     1740
ttaacgcgtc atatgggatc cccggagctt gggctgcagg tcgagggacc taataacttc    1800
gtatagcata cattatacga agttatatta agggttccgg atcgatcccc atcaagcttc    1860
gaattcatgg cttcgtaccc cggccatcaa cacgcgtctg cgttcgacca ggctgcgcgt    1920
tctcgcggcc atagcaaccg acgtacggcg ttgcgccctc gccggcagca agaagccacg    1980
gaagtccgcc cggagcagaa atgcccacg ctactgcggg tttatataga cggtcccac     2040 gggatgggga aaaccaccac cacgcaactg ctggtggccc tgggttcgcg cgacgatatc    2100
gtctacgtac ccgagccgat gacttactgg cgggtgctgg gggcttccga cacaatcgcg    2160
aacatctaca ccacacaaca ccgcctcgac caggtgagaa tatcggccgg gacgcggcg    2220 gtggtaatga caagcgccca gataacaatg ggcatgcctt atgccgtgac cgacgccgtt   2280
ctggctcctc atatcggggg ggaggctggg agctcacatg ccccgccccc ggccctcacc    2340
ctcatcttcg accgccatcc catcgccgcc ctcctgtgct acccgccgcg cggtaccttt    2400
atgggcagca tgacccccca ggccgtgctg gcgttcgtgg ccctcatccc gccgaccttg    2460
cccggcacca acatcgtgct tggggcccttt ccggaggaca gacacatcga ccgcctggcc    2520
aaacgccagc gccccggcga gcggctggac ctggctatgc tggctgcgat tcgccgcgtt    2580
tacgggctac ttgccaatac ggtgcggtat ctgcagtgcg gcgggtcgtg gcgggaggac    2640
tggggacagc tttcgggac ggccgtgccg ccccaggtg ccgagcccca gagcaacgcg      2700
ggcccacgac ccccatatcgg ggacacgtta tttaccctgt ttcgggcccc cgagttgctg   2760
gcccccaacg gcgacctgta taacgtgttt gcctgggcct tggacgtctt ggccaaacgc    2820
ctccgttcca tgcacgtctt tatcctggat tacgaccaat cgcccgccgg ctgccgggac    2880
gccctgctgc aacttacctc cgggatggtc cagacccacg tcaccacccc cggctccata    2940
ccgacgatat gcgacctggc gcgcacgtttt gcccgggaga tgggggaggc taacggatcc    3000
accggatcta gataactgat cataatcagc cataccacat ttgtagaggt tttacttgct    3060
ttaaaaaacc tcccacacct cccctgaac ctgaaacata aaatgaatgc aattgttgtt     3120
gttaacttgt ttattgcagc ttataatggt tacaaataaa gcaatagcat cacaaatttc    3180
acaaataaag cattttttttc actgcattct agttgtggtt tgtccaaact catcaatgta    3240
tcttaacgcg t                                                          3251
```

<210> SEQ ID NO 3
<211> LENGTH: 752
<212> TYPE: DNA
<213> ORGANISM: Artificial Sequence
<220> FEATURE:
<223> OTHER INFORMATION: DNA probe for Southern blotting

<400> SEQUENCE: 3

```
ctagcgctac cggtcgccac catggtgagc aagggcgagg agctgttcac cggggtggtg     60
cccatcctgg tcgagctgga cggcgacgta aacggccaca agttcagcgt gtccggcgag    120
ggcgagggcg atgccaccta cggcaagctg accctgaagt tcatctgcac caccggcaag    180
ctgcccgtgc cctggcccac cctcgtgacc accctgacct acggcgtgca gtgcttcagc    240
cgctaccccg accacatgaa gcagcacgac ttcttcaagt ccgccatgcc cgaaggctac    300
gtccaggagc gcaccatctt cttcaaggac gacggcaact acaagacccg cgccgaggtg    360
```

```
aagttcgagg gcgacaccct ggtgaaccgc atcgagctga agggcatcga cttcaaggag    420
gacggcaaca tcctggggca aagctggag tacaactaca acagccacaa cgtctatatc    480
atggccgaca agcagaagaa cggcatcaag gtgaacttca agatccgcca caacatcgag    540
gacggcagcg tgcagctcgc cgaccactac cagcagaaca cccccatcgg cgacggcccc    600
gtgctgctgc ccgacaacca ctacctgagc acccagtccg ccctgagcaa agaccccaac    660
gagaagcgcg atcacatggt cctgctggag ttcgtgaccg ccgccgggat cactctcggc    720
atggacgagc tgtacaagtc cggccggact ca                                  752
```

```
<210> SEQ ID NO 4
<211> LENGTH: 25
<212> TYPE: DNA
<213> ORGANISM: Artificial Sequence
<220> FEATURE:
<223> OTHER INFORMATION: PCR primer

<400> SEQUENCE: 4
accgagctcg gatccactag taacg                                          25

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ctcaccatgg tggcgaccgg                                                20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
gccccactca cctgctgcta                                                20

<210> SEQ ID NO 7
<211> LENGTH: 24
<212> TYPE: DNA
<213> ORGANISM: Artificial Sequence
<220> FEATURE:
<223> OTHER INFORMATION: PCR primer

<400> SEQUENCE: 7
tttacgggtc aacttcacat tcaa                                           24

<210> SEQ ID NO 8
<211> LENGTH: 17
<212> TYPE: DNA
<213> ORGANISM: Artificial Sequence
<220> FEATURE:
<223> OTHER INFORMATION: PCR primer

<400> SEQUENCE: 8
ctgctgcccg acaacca                                                   17

<210> SEQ ID NO 9
<211> LENGTH: 21
<212> TYPE: DNA
<213> ORGANISM: Artificial Sequence
```

```
<220> FEATURE:
<223> OTHER INFORMATION: PCR primer

<400> SEQUENCE: 9
gaactccagc aggaccatgt g                                              21

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
agaatgggaa gcttgtcatc                                                20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
gtagactcca cgacatactc                                                20

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
ctcacctgct gctactcatt c                                              21

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
gcttgaggtg gttgtggaaa a                                              21

<210> SEQ ID NO 14
<211> LENGTH: 23
<212> TYPE: DNA
<213> ORGANISM: Artificial Sequence
<220> FEATURE:
<223> OTHER INFORMATION: PCR primer

<400> SEQUENCE: 14
cctacggcgt gcagtgcttc agc                                            23

<210> SEQ ID NO 15
<211> LENGTH: 18
<212> TYPE: DNA
<213> ORGANISM: Artificial Sequence
<220> FEATURE:
<223> OTHER INFORMATION: PCR primer

<400> SEQUENCE: 15
tgctcaggta gtggttgt                                                  18
```

```
<210> SEQ ID NO 16
<211> LENGTH: 23
<212> TYPE: DNA
<213> ORGANISM: Artificial Sequence
<220> FEATURE:
<223> OTHER INFORMATION: PCR primer

<400> SEQUENCE: 16
gtggcaaagt ggagattgtt gcc                                              23

<210> SEQ ID NO 17
<211> LENGTH: 21
<212> TYPE: DNA
<213> ORGANISM: Artificial Sequence
<220> FEATURE:
<223> OTHER INFORMATION: PCR primer

<400> SEQUENCE: 17
gatgatgacc cgtttggctc c                                                21
```